(12) United States Patent
Pedain

(10) Patent No.: US 9,989,547 B2
(45) Date of Patent: Jun. 5, 2018

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Christoph Pedain, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days. days.

(21) Appl. No.: 15/405,432

(22) Filed: Jan. 13, 2017

(65) Prior Publication Data

US 2017/0131309 A1 May 11, 2017

Related U.S. Application Data

(63) Continuation of application No. PCT/EP2015/066915, filed on Jul. 23, 2015.

(30) Foreign Application Priority Data

Jul. 24, 2014 (EP) ..................................... 14178441

(51) Int. Cl.
*B65G 54/02* (2006.01)
*G01N 35/04* (2006.01)

(52) U.S. Cl.
CPC ............. *G01N 35/04* (2013.01); *B65G 54/02* (2013.01); *B65G 2201/0261* (2013.01); *G01N 2035/0477* (2013.01)

(58) Field of Classification Search
CPC ............ B65G 2201/0261; B65G 54/02; G01N 2036/00326; G01N 2035/0477
(Continued)

(56) References Cited

U.S. PATENT DOCUMENTS 3,273,727 A 9/1966 Rogers et al.
3,653,485 A 4/1972 Donlon
(Continued)

FOREIGN PATENT DOCUMENTS

CN 201045617 Y 4/2008
CN 102109530 A 6/2011
(Continued)

OTHER PUBLICATIONS

International Search Report dated Sep. 28, 2015, in Application No. PCT/EP2015/068915, 4 pages.

*Primary Examiner* — Douglas A Hess
(74) *Attorney, Agent, or Firm* — Roche Diagnostics Operations, Inc.

(57) ABSTRACT

A laboratory sample distribution system is presented. The system comprises sample container carriers carrying a sample container and comprising a magnetically active device. The system also comprises a transport plane supporting the sample container carriers and comprises drive modules comprising first line shaped conductors extending in a first direction and arranged parallel to each other and second line shaped conductors extending in a second direction and arranged parallel to each other. The system comprises a driver electrically connected to each of the first and second conductors of the drive modules. The driver selectively applies a drive current and/or voltage to the first and second conductors such that a conductor current results in the conductors driven by the drive current and/or voltage. The conductor current selectively causes a drive force to the sample container carriers such that the sample container carriers move along individual transport paths on the transport plane.

11 Claims, 1 Drawing Sheet

(58) Field of Classification Search
USPC ....... 198/340, 349, 358, 465.1, 619; 422/63,
422/65; 700/228, 230; 414/222.02,
414/222.13
See application file for complete search history.

(56) References Cited

U.S. PATENT DOCUMENTS

| | | |
|---|---|---|
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,264,111 B2 * | 9/2007 | Veiner .................... G01N 35/04 198/465.1 |
| 7,278,532 B2 | 10/2007 | Martin |
| 7,326,565 B2 | 2/2008 | Yokoi et al. |
| 7,425,305 B2 * | 9/2008 | Itoh .................... G01N 35/0099 422/547 |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,973,736 B2 * | 3/2015 | Johns .................... B01D 21/262 198/439 |
| 9,097,691 B2 | 8/2015 | Onizawa et al. |
| 9,187,268 B2 * | 11/2015 | Denninger ............. B65G 54/02 |
| 9,211,543 B2 | 12/2015 | Ohga et al. |
| 9,239,335 B2 * | 1/2016 | Heise .................... B65G 54/02 |
| 9,423,410 B2 | 8/2016 | Buehr |
| 9,423,411 B2 | 8/2016 | Riether |
| 9,593,970 B2 * | 3/2017 | Sinz .................... G01R 33/0035 |
| 9,618,525 B2 * | 4/2017 | Malinowski ........... G01N 35/04 |
| 9,658,241 B2 * | 5/2017 | Riether ............. G01N 35/1081 |
| 9,664,703 B2 * | 5/2017 | Heise .................... G01N 35/04 |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276780 A1 | 10/2015 | Riether et al. |
| 2015/0276781 A1 | 10/2015 | Riether et al. |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |

(56) References Cited

U.S. PATENT DOCUMENTS

| | | |
|---|---|---|
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | S63-82433 U | 5/1983 |
| JP | 60-223481 | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-290101 A | 11/1988 |
| JP | 1148966 | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A2 | 3/1993 |
| JP | H05-142232 A | 6/1993 |
| JP | H05-180847 A | 7/1993 |
| JP | 06-26808 | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A2 | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A2 | 2/2013 |
| JP | 2013-190400 A | 9/2013 |
| SU | 685591 A1 | 9/1979 |
| WO | 1996036437 A1 | 11/1996 |
| WO | 2003042048 A3 | 5/2003 |
| WO | 2007024540 A1 | 3/2007 |
| WO | 2008133708 A1 | 11/2008 |
| WO | 2009002358 A1 | 12/2008 |
| WO | 2010042722 A1 | 4/2010 |
| WO | 2012170636 A1 | 7/2010 |
| WO | 2010087303 A1 | 8/2010 |
| WO | 2010129715 A1 | 11/2010 |
| WO | 2012158520 A1 | 11/2012 |
| WO | 2012158541 A1 | 11/2012 |
| WO | 2013152089 A1 | 10/2013 |
| WO | 2013169778 A1 | 11/2013 |
| WO | 2013177163 A1 | 11/2013 |
| WO | 2014059134 A1 | 4/2014 |
| WO | 2014071214 A1 | 5/2014 |

\* cited by examiner

LABORATORY SAMPLE DISTRIBUTION SYSTEM AND LABORATORY AUTOMATION SYSTEM

CROSS-REFERENCE TO RELATED APPLICATIONS

This application is a continuation of PCT/EP2015/066915, filed Jul. 23, 2015, which is based on and claims priority to EP 14178441.3, filed Jul. 24, 2014, which is hereby incorporated by reference.

BACKGROUND

The present disclosure relates to a laboratory sample distribution system and a laboratory automation system.

Known laboratory sample distribution systems are typically used in laboratory automation systems in order to distribute samples contained in sample containers between different laboratory stations.

A typical laboratory sample distribution system provides for a high throughput and for reliable operation. The system uses single coils for driving sample container carriers on a surface. While single coils have the advantage of being able to position an object precisely over such coil, for example in a checkerboard pattern, this technology leads to increased size, weight, and effort to assemble.

Therefore, there is a need for a laboratory sample distribution system and a laboratory automation system being cost efficient and being easy to assemble.

SUMMARY

According to the present disclosure, a laboratory sample distribution system is presented. The laboratory sample distribution system can comprise a number of sample container carriers. The sample container carriers can each comprise at least one magnetically active device. The sample container carriers can be adapted to carry at least one sample container. The laboratory sample distribution system can also comprise a transport plane. The transport plane can be adapted to support the sample container carriers. The laboratory sample distribution system can also comprise a number of drive modules. Each of the drive modules can comprises a number of first line shaped conductors, wherein the first conductors extend in a first direction and wherein the first conductors are arranged parallel to each other, and a number of second line shaped conductors, wherein the second conductors extend in a second direction and wherein the second conductors are arranged parallel to each other. The laboratory sample distribution system can also comprise a driver. The driver can be electrically connected to the first and second conductors of the drive modules. The driver can be adapted to selectively apply a drive current and/or a drive voltage to one or more of the first and second conductors such that a conductor current results in the one or more conductors driven by the drive current and/or the drive voltage. The conductor current can selectively cause a drive force to one or more of the sample container carriers such that the sample container carriers move along individual transport paths on the transport plane.

Accordingly, it is a feature of the embodiments of the present disclosure to provide for a laboratory sample distribution system and a laboratory automation system being cost efficient and being easy to assemble. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
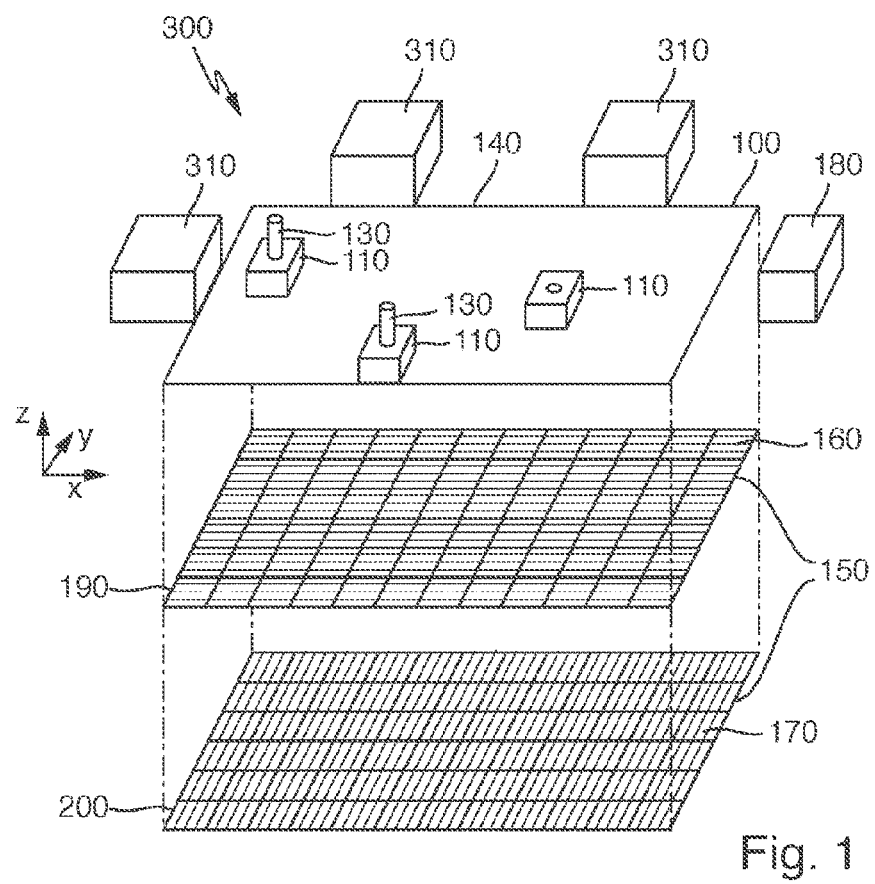
FIG. 1 illustrates a laboratory automation system comprising a laboratory sample distribution system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system can comprise a number of sample container carriers. The sample container carriers can each comprise at least one magnetically active device. The sample container carriers can be adapted to carry at least one sample container.

The laboratory sample distribution system can comprise a transport plane. The transport plane can be adapted to support the sample container carriers.

The sample containers can typically be designed as tubes made of glass or transparent plastic and can typically have an opening at an upper end. The sample containers can be used to contain, store and transport samples such as blood samples or chemical samples. The transport plane can also be denoted as transport surface. The transport plane can support the sample container carriers, what can also be denoted as carrying the sample container carriers.

The at least one magnetically active device in each sample container carrier may be a permanent magnet. Alternatively or additionally, an electro-magnet and/or any magnetically soft material can be used. The sample container carriers can typically be adapted to move in two dimensions on the transport plane.

The laboratory sample distribution system can comprise a number (e.g., 1 to 1000) of drive modules or grid elements. A respective drive module can comprise a number (1 to 1000) of first line shaped electrical conductors or tracks. In an operational mode, the first conductors can be arranged stationary below the transport plane. The first conductors can each extend in a first direction. The first conductors can be arranged substantially parallel to each other.

A respective drive module can further comprise a number (e.g., 1 to 1000) of second line shaped conductors or tracks. In an operational mode, the second conductors can be arranged stationary below the transport plane. The second conductors can each extend in a second direction different from the first direction. The second conductors can be arranged substantially parallel to each other.

The conductors may, for example, be regularly arranged spaced by a given distance, e.g. 1 mm to 50 mm, to one another.

The laboratory sample distribution system and/or a respective drive module can further comprise a driver. The driver is electrically connected to each of the first and second conductors of each of the drive modules. The electrical connection may be done in a parallel manner, i.e., the driver may have a corresponding drive terminal for each of the conductors. Alternatively, the electrical connection may be done in a timely sequential, or multiplexed, manner such that the number of necessary drive terminals can be reduced.

The driver can be adapted to apply a drive current and/or a drive voltage to a selection of one or more of the first and/or second conductors such that a conductor current can result in the one or more selected conductors driven by the drive current and/or the drive voltage. The conductor current can cause a magnetic drive force to one or more of the sample container carriers such that the sample container carriers move along individual transport paths on the transport plane. The conductors may be selectively driven by the driver such that a desired magnetic force can be caused, the magnetic force being directed in x-, y- and/or z-direction.

The first direction may be substantially perpendicular to the second direction.

The first conductors may be arranged in a first layer, or plane. The first layer, or plane, can be substantially parallel to the transport plane. The second conductors may be arranged in a second layer, or plane. The second layer, or plane, can be substantially parallel to the transport plane. The first and the second layer may be stacked.

The first conductors may be embodied as printed circuit board tracks on a first layer of a printed circuit board and the second conductors may be embodied as printed circuit board tracks on a second layer of the printed circuit board or another printed circuit board.

The sample container carriers may respectively comprise a plurality, e.g., four, six, or eight, of magnetically active devices or permanent magnets. Each of the magnetically active devices can comprise a one-dimensional Halbach array. The geometrical/magnetical structure of the Halbach array may be adapted to the geometrical structure (distance between) of the conductors.

The laboratory sample distribution system may comprise position detecting device. The position detecting device can be adapted to measure a current in one or more conductors and to detect the presence of a sample container carrier on top of the one or more conductors in response to the measured current.

The drive modules may be arranged adjacent to each other in the first and/or second direction to form a larger entity.

The laboratory automation system can comprise a number of pre-analytical, analytical and/or post-analytical laboratory stations and a laboratory sample distribution system described above can be adapted to distribute the sample container carriers and/or sample containers between the laboratory stations.

The laboratory stations may be arranged adjacent to the laboratory sample distribution system. Pre-analytical stations may be adapted to perform any kind of pre-processing of samples, sample containers and/or sample container carriers. Analytical stations may be adapted to use a sample, or part of the sample, and a reagent to generate a measuring signal. The measuring signal can indicate if and in which concentration, if any, an analyte exists. Post-analytical stations may be adapted to perform any kind of post-processing of samples, sample containers and/or sample container carriers. The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

A multi-layer printed circuit board for planar or spatial movement control of sample container carriers may be used. The present disclosure can allow for motion control utilizing drive modules that possess conductor tracks.

To detect the position of objects over the drive module, sensors can be applied. It is also possible to measure current induced by the magnetically active devices embedded into the sample container carriers.

A driver can control the movement of the sample container carriers concurrently.

To create larger surfaces and control motion of sample container carriers on those, multiple drive modules can be placed next to each other like tiles, and sample container carriers can be handed over from one drive module to the next. To achieve coordinated movement across boundaries of drive modules, multiple control units can communicate with one another.

The handover of sample container carriers from one drive module to another may be performed by anticipating the transport path that a sample container carrier may take on the entire transport plane. With this anticipation, the driver can ensure that such transport path can be cleared from other sample container carriers by moving those other sample container carriers away from such transport path, or by choosing a transport path that does not cross the pathways or positions of other sample container carriers. It can furthermore be possible to take the speeds and pathways of such sample container carriers into account to allow for routing sample container carriers with pre-defined relative distances to one another such that collisions can be avoided while optimal pathways for speedy or otherwise advantageous transport are chosen.

Handover from one drive module to another can be performed by activating one or more conductors on a second drive module in a fashion such that the speed of the sample container carrier can be maintained. The speed can be measured using position sensing equipment and timing the distance traveled by a sample container carrier between two or more of such position sensors. In one embodiment, the conductors themselves can be used as positioning sensors by measuring current introduced into a conductor.

Utilizing the so computed speed of an sample container carrier, the activation of a conductor on a second drive module can be timed such that the handover between drive modules can remain smooth and unwanted accelerations or decelerations can be avoided.

In the event of unsuccessful handover, i.e., if a sample container carrier is not sensed on the second drive module at the predicted time, error handling can occur. Such error handling may include de-activation of the second drive module, attempting to draw the sample container carrier back onto the first drive module until detected there, attempting to draw the sample container carrier to any neighboring drive module until detected there, applying secondary or tertiary position sensors to find the sample container carrier at an unexpected place, driving a detector mounted onto a movable object to the vicinity of the expected position until the sample container carrier is found, or triggering an alarm to ask for human intervention into the system for finding and repositioning the missing sample container carrier.

Driving sample container carrier in a fashion such that they span more than two drive modules at one time can be possible. For controlling such movement, handover and error handling as described above may span all of the affected drive modules. With such implementation, it may be possible to employ movement pathways that are described in the resolution of the tracks or conductors, not only in the more coarse resolution of the drive modules. It can further be possible to move sample container carriers that themselves are larger than one of the drive modules.

The laboratory sample distribution system may be arranged to cause a planar or spatial movement of the sample container carriers.

According to a method to control the movement of sample container carriers in the system as described above lifting, holding and moving of the sample container carriers may be achieved by dynamically deciding about the driving of the conductors based on one or more of the following factors: power consumption, need for mechanical stability of position due to operations carried out on or with the sample container carriers, desired speed of movement, desired degree of parallelism of movements of multiple sample container carriers, desired positive acceleration, desired negative acceleration.

Tile information may be transmitted to the drive modules about sample container carriers approaching a boundary of a drive module, receiving the information from the drive module about the readiness to receive the sample container carrier, and powering the drive modules in a manner that exerts a constant drive force onto the sample container carrier.

The information communicated between the drive modules may include one or more of the following: speeds, current position, movement target coordinates.

Referring initially to FIG. 1, FIG. 1 shows a laboratory automation system 300, comprising a number of pre-analytical, analytical and/or post-analytical laboratory stations 310 and a laboratory sample distribution system 100 adapted to distribute sample container carriers 110 and/or sample containers 130 between the laboratory stations 310. Self-evidently, more than the depicted laboratory stations 310 may be comprised in the laboratory automation system 300.

Figure 2:
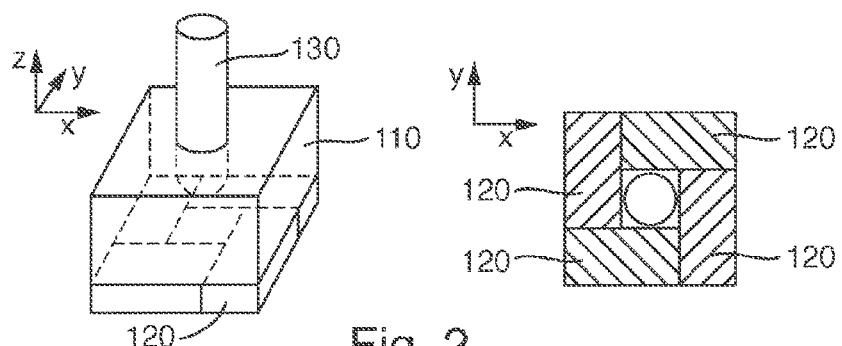
FIG. 2 illustrates a sample container carrier of the laboratory automation system of FIG. 1 in more detail according to an embodiment of the present disclosure.

Referring now to FIG. 2, the sample container carriers 110 can each comprise four magnetically active devices in form of four one-dimensional Halbach arrays 120 having a different orientation, as depicted.

The laboratory sample distribution system 100 can further comprise a transport plane 140. The transport plane 140 can be adapted to support the sample container carriers 110.

The laboratory sample distribution system 100 can further comprise a number of drive modules 150 having a substantially rectangular shape and being positioned directly adjacent to one another under the transport plane 140. The transport plane 140 can cover the arrangement of the number of drive modules 150.

The drive modules 150 can comprise a number of first line shaped electrical conductors, or tracks, 160. The first conductors 160 can be arranged stationary below the transport plane 140. The first conductors 160 can extend in a first direction x. The first conductors 160 can be arranged substantially parallel to each other.

The drive modules 150 can comprise a number of second line shaped electrical conductors, or tracks, 170. The second conductors 170 can be arranged stationary below the transport plane 140. The second conductors 170 can extend in a second direction y substantially perpendicular to the first direction x. The second conductors 170 can be arranged substantially parallel to each other.

The laboratory sample distribution system 100 can further comprise an electrical driver 180. The driver 180 can be electrically connected to each of the first and second conductors 160, 170 of each of the drive modules 150. The driver 180 can be adapted to apply a drive current and/or a drive voltage to one or more of the first and second conductors 160, 170, such that a conductor current can be caused in the one or more conductors 160, 170 driven by the drive current and/or the drive voltage. The conductor current can selectively cause a drive force to one or more of the sample container carriers 110 such that the sample container carriers 110 can move along individual transport paths on the transport plane 140. The conductors 160, 170 being driven can be selected in response to the position of the sample container carriers 110 and the desired transport path of the sample container carriers 110 such that a corresponding desired magnetic drive force can be applied to each of the sample container carriers 110.

Figure 3:
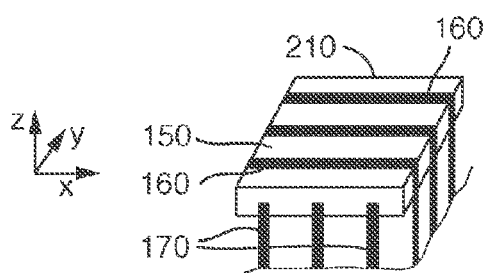
FIG. 3 illustrates partially a drive module of the laboratory automation system of FIG. 1 in more detail according to an embodiment of the present disclosure.

Referring to FIG. 3, the first conductors 160 can be arranged as printed circuit board tracks on a first layer 190 of a printed circuit board 210 and the second conductors 160 can be arranged as printed circuit board tracks on a second layer 200 of the printed circuit board 210.

The conductors 160, 170 formed on the printed circuit board 210 may be electrically contacted at the edge of the printed circuit board 210. Electrical wires may be electrically connected to the conductors 160, 170. The electrical wires can be electrically connected to the driver 180.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
a number of sample container carriers, wherein the sample container carriers each comprise at least one magnetically active device and wherein the sample container carriers are adapted to carry at least one sample container;

a transport plane, wherein the transport plane is adapted to support the sample container carriers;

a number of drive modules, wherein each of the drive modules comprises,
- a number of first line shaped conductors, wherein the first conductors extend in a first direction and wherein the first conductors are arranged parallel to each other, and
- a number of second line shaped conductors, wherein the second conductors extend in a second direction and wherein the second conductors are arranged parallel to each other; and a driver, wherein the driver is electrically connected to the first and second conductors of the drive modules, wherein the driver is adapted to selectively apply a drive current and/or a drive voltage to one or more of the first and second conductors such that a conductor current results in the one or more conductors driven by the drive current and/or the drive voltage, wherein the conductor current selectively causes a drive force to one or more of the sample container carriers such that the sample container carriers move along individual transport paths on the transport plane.

2. The laboratory sample distribution system according to claim 1, wherein the first direction is perpendicular to the second direction.

3. The laboratory sample distribution system according to claim 1, wherein the first conductors are arranged in a first layer and wherein the first layer is parallel to the transport plane.

4. The laboratory sample distribution system according to claim 1, wherein the second conductors are arranged in a second layer and wherein the second layer is parallel to the transport plane.

5. The laboratory sample distribution system according to claim 1, wherein the first conductors are embodied as printed circuit board tracks on a first layer of a printed circuit board.

6. The laboratory sample distribution system according to claim 5, wherein the second conductors are embodied as printed circuit board tracks on a second layer of the printed circuit board.

7. The laboratory sample distribution system according to claim 1, wherein the sample container carriers each comprise a plurality of magnetically active devices.

8. The laboratory sample distribution system according to claim 7, wherein each of the magnetically active devices comprises a one-dimensional Halbach array.

9. The laboratory sample distribution system according to claim 1, further comprising,
a position detecting device, wherein the position detecting device is adapted to measure a current in one or more conductors and to detect the presence of a sample container carrier on top of the one or more conductors in response to the measured current.

10. The laboratory sample distribution system according to claim 1, wherein the number of drive modules is arranged adjacent to each other in the first and/or second direction.

11. A laboratory automation system, the laboratory automation system comprising:
a number of pre-analytical, analytical and/or post-analytical laboratory stations; and
a laboratory sample distribution system according to claim 1 adapted to distribute the sample container carriers and/or sample containers between the laboratory stations.

* * * * *